(12) United States Patent
Pruche et al.

(10) Patent No.: US 6,380,263 B1
(45) Date of Patent: Apr. 30, 2002

(54) 6-SUBSTITUTED PYRIMIDINE 3-OXIDES FOR PROMOTING PIGMENTATION OF THE SKIN/HAIR

(75) Inventors: Francis Pruche, Paris; Catherine Gerst, Asnieres/Seine, both of (FR)

(73) Assignee: Societe L'Oreal, Paris (FR)

( * ) Notice: Subject to any disclaimer, the term of this patent is extended or adjusted under 35 U.S.C. 154(b) by 0 days.

(21) Appl. No.: 08/931,890

(22) Filed: Sep. 17, 1997

(30) Foreign Application Priority Data

Sep. 17, 1996 (FR) ............................................. 96 11316

(51) Int. Cl.[7] .................. A61P 17/31; A61K 31/505; A61K 7/021; A61K 7/13
(52) U.S. Cl. ...................... 514/880; 514/275; 424/70.6; 424/63; 424/59
(58) Field of Search ............................ 424/59, 63, 70.6; 514/275, 880, 887

(56) References Cited

PUBLICATIONS

STN, Serveur de Bases de Donnees, XP002029091, Karlsruhe, DE, Fichier Embase, AN: 94237812.
STN, Serveur de Bases de Donnees, XP002029092, Karlsruhe, DE, Fichier Embase, AN: 90117315.
STN, Serveur de Bases de Donnees, XP002029093, Karlsruhe, DE, Fichier Medline, AN: 83184944.
Database WPI, Week 8647, Derwent Publications Ltd., London, GB, AN 86–308507, XP002029095 & JP 61 227 518 A (Kanebo).
STN, Serveur de Bases de Donnees, XP002029094, Karlsruhe, DE, Fichier Medline, AN: 90030985 & Clin. Exp. Dermatol . . . "quantative assessment of 2% topical minoxidil in the treatment of male pattern baldness".

*Primary Examiner*—Edward J. Webman
*Assistant Examiner*—Helen Nguyen
(74) *Attorney, Agent, or Firm*—Burns, Doane, Swecker & Mathis, L.L.P.

(57) ABSTRACT

Pigmentation of human skin and/or hair is promoted by administering to individuals in need of such treatment, advantageously topically, an effective tyrosinase activity-stimulating amount of at least one 6-substituted pyrimidine 3-oxide having the structural formula (I):

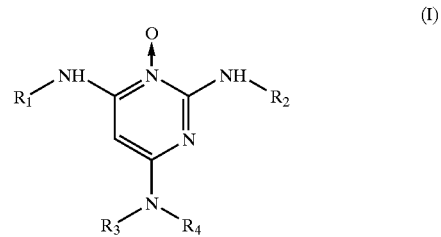

in which $R_1$ and $R_2$, which may be identical or different, are each a hydrogen atom or a $C_1$–$C_{12}$ alkyl radical; and $R_3$ and $R_4$, which may be identical or different, are each a $C_1$–$C_{12}$ alkyl radical or, when taken together, form a heterocycle with the nitrogen atom from which they depend, with the proviso that, when $R_3$ and $R_4$, taken together, form a piperidino ring, then at least one of the radicals $R_1$ or $R_2$ must be other than a hydrogen atom.

7 Claims, No Drawings ns
6-SUBSTITUTED PYRIMIDINE 3-OXIDES FOR PROMOTING PIGMENTATION OF THE SKIN/HAIR

BACKGROUND OF THE INVENTION

1. Technical Field of the Invention

The present invention relates to promoting pigmentation of the skin and/or the hair by administering to individuals in need of such treatment at least one pyrimidine 3-oxide derivative, substituted in position 6, and to pharmaceutical/cosmetic compositions comprising at least one such derivative.

2. Description of the Prior Art

The color of human hair and skin depends on various factors and, in particular, the seasons of the year, race, sex and age. It is principally determined by the concentration of melanin produced by the melanocytes. The melanocytes are specialized cells which synthesize melanin by means of specific organelles, the melanosomes.

The synthesis of melanin, or melanogenesis, is particularly complex and schematically involves the following principal steps:

Tyrosine→Dopa→Dopaquinone→Dopachrome→Melanin

Tyrosinase (monophenol dihydroxyl phenylalanine:oxygen oxidoreductase EC 1.14.18.1) is the essential enzyme involved in this reaction sequence. It catalyzes, in particular, the reaction for the conversion of tyrosine into dopa (dihydroxyphenyl-alanine) and the reaction for the conversion of dopa into dopaquinone.

Although the level of melanin varies from one population to another, the amount of tyrosinase does not vary significantly and the level of messenger RNAs for tyrosinase is identical in white or black skin. The variations in melanogenesis are thus due to variations in the activity of tyrosinase.

It is known that in most populations the brown coloration of the skin and the maintenance of a constant color of the hair are important aspirations.

There are, moreover, pigmentation diseases such as, for example, vitiligo, which is an autoimmune disease characterized by the appearance of white patches on the skin, associated with a pigmentation defect.

Genuine need therefore exists for products which facilitate and/or improve pigmentation of the skin and/or the hair.

In this respect, many artificial dyeing techniques have been proposed to this art, by supplying external dyes that are intended to impart to the skin and/or the hair the closest possible color to their natural color, as well as natural dyeing techniques by stimulation of the natural pigmentation route.

Although, admittedly, excellent results are obtained by the solutions proposed in the prior art, it nevertheless remains that the stimulation of pigmentation of the skin and/or the hair via the natural route remains the ideal route for pigmentation.

In this regard, WO-A-95/17,161, WO-95/11,003, WO-A-95/01,773, WO-A-94/04,674, WO-A-94/04,122,
EP-A-585,018, WO-A-93/10,804, WO-A-92/20,322 and WO-A-91/07,945 describe varied techniques for attaining the desired results, such as administration of compositions containing phosphodiesterase inhibitors, prostaglandins, DNA fragments, or tyrosine derivatives or, alternatively, administration of plant extracts.

Often, the compounds used have appreciable side-effects or are complex mixtures which have no specificity.

It has also been suggested, by Rushton and co-workers (Rushton, D. H., et coll., *Clin. Exp. Dermatol.*, 14(1), 40–46 (1989)) that Minoxidil, or 2,4-diamino-6-piperidinopyrimidine 3-oxide, can exhibit a stimulatory effect on hair pigmentation in bald men treated with this compound.

"Minoxidil" is known for its anti-hypertensive effects and for its capacity to promote hair growth. These properties are described in U.S. Pat. No. 4,596,812.

Although Minoxidil remains the reference compound in the field of hair growth, it has appreciable side-effects which complicate its use.

Thus, developing novel active agents which affect skin and/or hair pigmentation without eliciting undesirable side-effects remains a major research objective.

SUMMARY OF THE INVENTION

Accordingly, a major object of the present invention is the provision of novel compounds to promote pigmentation of the skin and/or the hair, while at the same time limiting deleterious side effects.

Briefly, it has now unexpectedly been determined that certain pyrimidine 3-oxide derivatives, substituted in position 6, display an activating effect on tyrosinase which is similar or superior to that of Minoxidil.

The subject compounds according to the invention have the following structural formula (I):

$$R_1\text{-NH} \underset{}{\overset{}{\diagup}} \text{pyrimidine 3-oxide with } NH\text{-}R_2, N\text{-}R_3R_4 \text{ substituents} \quad (I)$$

in which $R_1$ and $R_2$, which may be identical or different, are each a hydrogen atom or a $C_1$–$C_{12}$ alkyl radical; and $R_3$ and $R_4$, which may be identical or different, are each a $C_1$–$C_{12}$ alkyl radical or, when taken together, form a heterocycle with the nitrogen-atom from which they depend, with the proviso that, when $R_3$ and $R_4$, taken together, form a piperidino ring, then at least one of the radicals $R_1$ or $R_2$ must be other than a hydrogen. atom.

DETAILED DESCRIPTION OF BEST MODE AND SPECIFIC/PREFERRED EMBODIMENTS OF THE INVENTION

More particularly according to the present invention, featured are cosmetic/pharmaceutical compositions comprising, as the active principle, an effective amount of at least one pyrimidine 3-oxide compound, substituted in position 6 and having the formula (I), for promoting pigmentation of the skin and/or the hair.

The present invention also features cosmetic/pharmaceutical compositions comprising, as the active principle, an effective amount of at least one pyrimidine 3-oxide compound, substituted in position 6 and having the formula (I), for stimulating tyrosinase activity, and formulated into a cosmetically/pharmaceutically acceptable vehicle, diluent or carrier therefor.

This invention also features use of the optical isomers of the subject compounds, singly or in admixture in all proportions, as well as use of the acyl derivatives or pharmaceutically acceptable salts thereof.

According to the invention, by the expression "$C_1$–$C_{12}$ alkyl radical" is intended linear or branched $C_1$–$C_{12}$ alkyl radicals, optionally substituted with at least one hydroxyl radical or benzyl radical and, in particular, the optionally substituted linear or branched methyl, ethyl, propyl, butyl, pentyl, hexyl or benzyl radicals.

By the term "heterocycle" is intended any saturated or unsaturated ring member containing at least one nitrogen atom, including, in particular, aziridino, azetidino, pyrrolidino, piperidino, hexamethyleneimino, heptamethyleneimino, octamethyleneimino, tetrahydropyridino, dihydropyridino, pyrrole, pyrazole, imidazole, triazole, 4-alkylpiperazino, morpholino or thiomorpholino rings members.

According to the invention, the heterocycle is preferably a piperidino ring member.

Of course, the derivatives of formula (I) may be administered either alone or as a mixture in any proportion.

By the term "tyrosinase" is intended any enzyme exhibiting tyrosinase activity, it being possible for this enzyme to exhibit other enzymatic activities.

The tyrosinase activity may be defined as the enzymatic activity which catalyzes the oxidation of tyrosine resulting in the formation of the melanin precursor: dopaquinone.

Many pyrimidine derivatives substituted in position 6 and techniques for the synthesis thereof are known to this art. Particularly exemplary are those described in EP-A-353,123, EP-A-356,271, EP-A-408,422, EP-A-420,707, EP-A-427,625, EP-A-459,890, EP-A-519,819, EP-A-522,964, EP-A-525,964 and EP-A-540,629.

Among the 6-substituted pyrimidine 3-oxide compounds according to the invention, particularly preferred are:
2,4 bis-methylamino-6-dimethylaminopyrimidine 3-oxide,
2,4 bis-ethylamino-6-dimethylaminopyrimidine 3-oxide,
2,4-bis-propylamino-6-dimethylaminopyrimidine 3-oxide,
2,4-bis-propylamino-6-piperidinopyrimidine 3-oxide,
2-amino-4-methylamino-6-piperidinopyrimidine 3-oxide,
2-amino-4-propylamino-6-piperidinopyrimidine 3-oxide,
2-amino-4-hexylamino-6-piperidinopyrimidine 3-oxide,
2-amino-4-benzylamino-6-piperidinopyrimidine 3-oxide,
2-amino-4-(2-hydroxyethylamino)-6-piperidinopyrimidine 3-oxide,
2-amino-4-propylamino-6-dimethylaminopyrimidine 3-oxide,
2-amino-4-butylamino-6-dimethylaminopyrimidine 3-oxide,
2-amino-4-isopropylamino-6-dimethylaminopyrimidine 3-oxide.

Even more preferred are:
2-amino-4-propylamino-6-dimethylaminopyrimidine 3-oxide,
2-amino-4-methylamino-6-piperidinopyrimidine 3-oxide,
2,4-bis-propylamino-6-dimethylaminopyrimidine 3-oxide,
2,4-bis-propylamino-6-piperidinopyrimidine 3-oxide,
2,4-bis-methylamino-6-dimethylaminopyrimidine 3-oxide,
2,4-bis-ethylamino-6-dimethylaminopyrimidine 3-oxide.

The amount of compound required to promote pigmentation of the skin and/or the hair is an amount required to stimulate the tyrosinase activity. This amount is, of course, dependent on the nature of the derivative and on the nature of the tyrosinase in question and may vary over a wide range.

In order to provide an order of magnitude, if the derivative according to the invention is used in a cosmetic composition, the amount of derivative which is advantageously used may range from 0.01% to 20% of the total weight of the composition and preferably from 0.1% to 10% of the total weight of the composition.

In order to provide an order of magnitude, if the derivative according to the invention is used in a pharmaceutical composition, the amount of derivative which is advantageously used may range from 1% to 30% of the total weight of the composition and preferably from 2% to 15% of the total weight of the composition.

The compositions according to the invention are essentially intended to promote pigmentation of the skin and/or the hair and to stimulate the endogenous tyrosinase activity of the skin and/or the hair.

Thus, this invention features a cosmetic or pharmaceutical composition comprising at least one derivative corresponding to the structural formula (I) and at least one substrate of at least one enzyme exhibiting a tyrosinase activity.

Among the substrates which are suitable according to the invention, exemplary are tyrosine and derivatives thereof, and 3,4-dihydroxy-α-phenylalanine (DOPA).

It is possible to combine the derivative of formula (I) and the substrate in a single composition. However, other specific embodiments are intended, in particular the derivative and the substrate may be administered simultaneously, separately or variously over time.

Thus, the present invention features a product comprising at least one derivative corresponding to the structural formula (I) and at least one substrate of at least one enzyme exhibiting a tyrosinase activity, as a combination product for a simultaneous or separate use, or for use divided or spread out over time, in order to promote pigmentation of the skin and/or the hair.

In a specific embodiment, the derivative and the substrate may be packaged separately in the form of a kit whose components will be mixed together at the time of use.

The invention thus also features a kit comprising at least one derivative corresponding to the structural formula (I) and at least one substrate of at least one enzyme exhibiting a tyrosinase activity for simultaneous or separate use, or for use spread out over time, in order to promote pigmentation of the skin and/or the hair.

The compositions according to the invention may be ingested, injected or topically applied to the skin (onto any area of body skin) or the hair. According to the particular mode of administration, the compositions according to the invention may be in any pharmaceutical form normally used.

For topical application to the skin, the composition may be in the form, in particular, of an aqueous or oily solution or of a dispersion of the lotion or serum type, emulsions of liquid or semi-liquid consistency of the milk type, obtained by dispersion of a fatty phase in an aqueous phase (O/W) or, conversely, (W/O), or suspensions or emulsions of soft consistency of the cream or aqueous or anhydrous gel type, or alternatively microcapsules or microparticles, or vesicle dispersions of the ionic and/or nonionic type. These compositions are formulated according to the usual techniques.

They may also be applied to the hair in the form of aqueous, alcoholic or aqueous-alcoholic solutions, or in the form of creams, gels, emulsions or mousses or alternatively in the form of aerosol compositions also comprising a propellant under pressure.

The compositions according to the invention may also be compositions for hair care, and in particular a shampoo, a hair-setting lotion, a treating lotion, a styling cream or gel, a composition for dyeing (in particular oxidation dyeing)

optionally in the form of dye shampoos, restructuring lotions for the hair, a permanent-wave composition (in particular a composition for the first stage of a permanent-wave operation), a lotion or gel to combat hair loss, an antiparasitic shampoo, etc.

For injection, the subject compositions may be formulated as an aqueous or oily lotion or as a serum, and for ingestion, they may be formulated as capsules, granules, syrups or tablets.

The amounts of the various constituents of the compositions according to the invention are those conventionally used in the particular fields under consideration.

The compositions according to the invention may also be formulated as solid preparations constituting cleansing soaps or bars.

The subject compositions may also be packaged in the form of an aerosol composition, also comprising a propellant under pressure.

When the composition is an emulsion, the proportion of the fatty phase advantageously ranges from 5% to 80% by weight, and preferably from 5% to 50% by weight, relative to the total weight of the composition. The oils, waxes, emulsifiers and co-emulsifiers formulated into the composition in emulsion form are selected from among those conventionally used in the cosmetics field. The emulsifier and the co-emulsifier are advantageously present in the composition in a proportion ranging from 0.3% to 30% by weight, and preferably from 0.5 to 20% by weight, relative to the total weight of the composition. The emulsion may also contain lipid vesicles.

When the composition is an oily gel or solution, the fatty phase may constitute more than 90% of the total weight of the composition.

In known manner, the cosmetic compositions may also contain additives and adjuvants that are conventional in the cosmetics field, such as hydrophilic or lipophilic gelling agents, hydrophilic or lipophilic additives, preservatives, antioxidants, solvents, fragrances, fillers, UV-screening agents, odor absorbers and colorants and dyestuffs. The amounts of these various additives and adjuvants are those conventionally used in the cosmetics field, and, for example, advantageously range from 0.01% to 10% of the total weight of the composition. Depending on their nature, these additives and adjuvants may be introduced into the fatty phase, into the aqueous phase and/or into the lipid spherules.

Exemplary such oils or waxes according to the invention include mineral oils (liquid petroleum jelly), plant oils (liquid fraction of karite butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) may be added to these oils. Exemplary emulsifiers according to the invention include glyceryl stearate, polysorbate 60 and the mixture of PEG-6/PEG-32/glycol stearate marketed under the trademark Tefose$^R$ 63 by Gattefosse.

And exemplary solvents include the lower alcohols and, in particular, ethanol and isopropanol, and propylene glycol.

Exemplary hydrophilic gelling agents according to the invention include carboxyvinyl polymers (carbomer), acrylic copolymers such as copolymers of acrylates/alkyl acrylates, polyacrylamides, polysaccharides such as hydroxypropylcellulose, natural gums and clays, and exemplary lipophilic gelling agents include modified clays such as bentones, metal salts of fatty acids such as aluminum stearates and hydrophobic silica, ethylcellulose and polyethylene.

The subject compositions may contain other hydrophilic active agents such as proteins or protein hydrolysates, amino acids, polyols, urea, allantoin, sugars and sugar derivatives, water-soluble vitamins, plant extracts and hydroxy acids.

Representative lipophilic active agents include retinol (vitamin A) and derivatives thereof, tocopherol (vitamin E) and derivatives thereof, essential fatty acids, ceramides, essential oils and salicylic acid and derivatives thereof.

According to the invention, the subject compositions may combine at least one compound of formula (I) with other active agents. Among these active agents, particularly exemplary are:

(a) agents which improve activity in respect of regrowth and/or retarding the loss of hair, already known to this art for this activity, such as, for example, nicotinic acid esters, including, in particular, tocopheryl nicotinate, benzyl nicotinate and $C_1$–$C_6$ alkyl nicotinates such as methyl or hexyl nicotinate, agents which promote the regrowth of hair, such as those described in EP-0,648,488, assigned to the assignee hereof;

(b) agents which decrease differentiation and/or proliferation, such as retinoic acid and isomers thereof, retinol and esters thereof, vitamin D and derivatives thereof, and estrogens such as estradiol;

(c) antibacterial agents such as clindamycin phosphate, erythromycin or antibiotics of the tetracyclin class;

(d) antiparasitic agents, in particular metronidazole, crotamiton or pyrethroids;

(e) antifungal agents, in particular compounds of the imidazole class such as econazole, ketoconazole or miconazole or salts thereof, polyene compounds such as amphotericin B, compounds of the allylamine family such as terbinafine, or, alternatively, octopirox;

(f) antiviral agents such as acyclovir;

(g) steroidal anti-inflammatory agents such as hydrocortisone, betamethasone valerate or clobetasol propionate, or nonsteroidal anti-inflammatory agents such as, for example, ibuprofen and salts thereof, diclofenac and salts thereof, acetylsalicylic acid, acetaminophene or glycyrrhizic acid;

(h) anaesthetics such as lidocaine hydrochloride and derivatives thereof;

(i) antipruriginous agents such as thenaldine, trimeprazine or cyproheptadine;

(j) keratolytic agents such as α- and β-hydroxycarboxylic acids or β-ketocarboxylic acids, and the salts, amides or esters thereof and, more particularly, hydroxy acids such as glycolic acid, lactic acid, salicylic acid, citric acid and fruit acids in general, and 5-n-octanoylsalicylic acid;

(k) anti-free-radical agents such as α-tocopherol and esters thereof, superoxide dismutases, certain metal-chelating agents or ascorbic acid and esters thereof;

(l) antiseborrhoeic agents such as progesterone;

(m) antidandruff agents such as octopirox or zinc pyrithione;

(n) antiacne agents such as retinoic acid or benzoyl peroxide;

(o) extracts of plant or bacterial origin.

Other such compounds include, for example, Diazoxide, Spiroxazone, phospholipids such as lecithin, linoleic acid, linolenic acid, salicylic acid and derivatives thereof described in FR-2,581,542, e.g., salicylic acid derivatives bearing an alkanoyl group having from 2 to 12 carbon atoms in position 5 of the benzene ring, hydroxycarboxylic or ketocarboxylic acids and their esters, lactones and their corresponding salts, anthralin, carotenoids, eicosatetraynoic and eicosatriynoic acids or the esters and amides thereof, vitamin D and derivatives thereof, and extracts of plant or bacterial origin.

Thus, in a preferred embodiment the subject compositions according to the invention also comprise at least one active agent selected from among antibacterial agents, antiparasitic agents, antifungal agents, antiviral agents, anti-inflammatory agents, antipruriginous agents, anaesthetics, keratolytic agents, anti-free-radical agents, antiseborrhoeic agents, antidandruff agents, antiacne agents and/or agents for reducing skin differentiation and/or proliferation and/or pigmentation, and extracts of plant or bacterial origin.

The subject compositions may also comprise at least one active agent as described above is in liposomal form, in particular as described in WO-94/22468, filed Oct. 13, 1994 by Anti-Cancer Inc. Thus, the compound encapsulated in the liposomes may be delivered selectively to the hair follicle.

The pharmaceutical compositions according to the invention may be administered parenterally, systemically, enterally or topically. These pharmaceutical compositions are preferably administered topically.

In order to determine the activity of the pyrimidine derivatives substituted in position 6, the simple and rapid technique is employed that entails measurement by incubating an optionally purified tyrosinase and one of its substrates in a suitable medium in the presence of a test compound, and then comparing the measurements taken with the results of identical measurements taken during the incubation of optionally purified tyrosinase with one of its substrates in the absence of the test compound.

In order to further illustrate the present invention and the advantages thereof, the following specific examples are given, it being understood that same are intended only as illustrative and in nowise limitative.

EXAMPLE 1

Modulation of Tyrosinase Activity by Pyrimidine 3-oxide Derivatives, Substituted in Position 6

General Principles of the Measurement:

A purified tyrosinase was incubated in the presence of one of its substrates in a suitable medium, in the presence or absence of a pyrimidine 3-oxide derivative, substituted in position 6. The activity of the enzyme was evaluated by measuring the amount of a product of conversion of the substrate formed during the reaction. The result obtained in the presence of a derivative was compared with the result obtained in the absence of a derivative.

This comparison made it possible to evaluate the influence of a derivative on the activity of the enzyme.

Preparation for the Measurements:

The substrate used was L-tyrosine (marketed by Sigma), a stock solution of which was prepared in phosphate-buffered saline (PBS) at a concentration of 0.5 mM.

The enzyme used was a purified fungal tyrosinase (EC 1.14.18.1) marketed by Sigma. A stock solution of this enzyme was prepared in PBS at a concentration of 5 mg/ml, which represents a concentration of about 19,500 international units of tyrosinase per milliliter.

The product of conversion of the tyrosine by tyrosinase, dopachrome, was measured by spectrophotometry at a wavelength of 475 nm using a Perkin Elmer type apparatus.

The derivative to be tested was prepared in solution in PBS containing 1% ethanol at a concentration of 1 mM.

Measurements:

The following reagents were mixed together in a spectrophotometer cell:

500 μl of tyrosine solution,

390 μl of phosphate buffer,

10 μl of fungal tyrosinase solution,

100 μl of solution of test derivative or of PBS/1% ethanol (control).

The mixture was then incubated at a temperature of 37° C. and the dopachrome formed was measured continuously for at least 30 minutes.

Results:

The results obtained are expressed as a % of activation of the tyrosinase activity relative to the value obtained with the control (in the absence of derivative).

| Derivatives | Activation |
|---|---|
| Control | 0% |
| 2,4-diamino-6-piperidinopyrimidine 3-oxide (Minoxidil) | 41% |
| 2,4-bis-methylamino-6-dimethylaminopyrimidine 3-oxide | 61% |
| 2,4-bis-ethylamino-6-dimethylaminopyrimidine 3-oxide | 60% |
| 2,4-bis-propylamino-6-dimethylaminopyrimidine 3-oxide | 55% |
| 2,4-bis-propylamino-6-piperidinopyrimidine 3-oxide | 57% |
| 2-amino-4-methylamino-6-piperidinopyrimidine 3-oxide | 50% |
| 2-amino-4-propylamino-6-piperidinopyrimidine 3-oxide | 46% |
| 2-amino-4-hexylamino-6-piperidinopyrimidine 3-oxide | 47% |
| 2-amino-4-benzylamino-6-piperidinopyrimidine 3-oxide | 45% |
| 2-amino-4-(2-hydroxyethylamino)-6-piperidinopyrimidine 3-oxide | 43% |
| 2-amino-4-propylamino-6-dimethylaminopyrimidine 3-oxide | 50% |
| 2-amino-4-butylamino-6-dimethylaminopyrimidine 3-oxide | 51% |
| 2-amino-4-isopropylamino-6-dimethylaminopyrimidine 3-oxide | 46% |

These results evidence that the pyrimidine derivatives, substituted in position 6, tested have stimulatory properties on tyrosinase which are superior to Minoxidil.

EXAMPLE 2

Specific Examples of Compositions of the Invention Containing an aryl 2,4-dioxooxazolidine (these compositions were formulated via the usual techniques currently employed in cosmetics or pharmacy)

| Dermal cream: | |
|---|---|
| 2,4-Bis-propylamino-6-piperidinopyrimidine 3-oxide | 1,000 g |
| Ceteareth 30 | 7,000 g |
| Glyceryl stearate | 2,000 g |
| Cetyl alcohol | 1,500 g |
| Polydimethylsiloxane | 1,500 g |
| Liquid petroleum jelly | 15,000 g |
| Pure glycerol codex | 20,000 g |
| Preservatives q.s. | |
| Demineralized water q.s. | 100,000 g |
| Dermal lotion to be sprayed: | |
| 2,4-Bis-methylamino-6-dimethylaminopyrimidine 3-oxide | 5,000 g |
| Ethanol | 30,000 g |
| Demineralized water q.s. | 100,000 g |
| Lotion for the hair: | |
| 2,4-Bis-ethylamino-6-dimethylaminopyrimidine 3-oxide | 3,000 g |

-continued

| Propylene glycol | 30,000 g |
|---|---|
| Ethylene alcohol | 40,500 g |
| Water qs | 100,000 g |

This lotion was applied to the scalp, once or twice a day, at a rate of 1 ml per application.

| Thickened lotion: | |
|---|---|
| 2,4-Bis-propylamino-6-piperidinopyrimidine 3-oxide | 5,000 g |
| Kawaine | 2,000 g |
| Hydroxypropylcellulose (Klucel G marketed by Hercules) | 3,500 g |
| Ethyl alcohol qs | 100,000 g |

This thickened lotion was applied to the scalp, once or twice a day, at a rate of 1 ml per application.

| Niosomal lotion: | |
|---|---|
| Chimexane NL ® | 0.475 g |
| Cholesterol | 0.475 g |
| Monosodium stearoylglutamate | 0.050 g |
| 2,4-Bis-propylamino-6-piperidinopyrimidine 3-oxide | 0.100 g |
| Preservatives qs | |
| Dyes qs | |
| Fragrance qs | |
| Demineralized water qs | 100,000 g |

This lotion was applied to the scalp, once or twice a day, at a rate of 1 ml per application.

| Lotion: | |
|---|---|
| 2,4-Bis-propylamino-6-dimethylaminopyrimidine 3-oxide | 5,000 g |
| Propylene glycol monomethyl ether (Dowanol PM marketed by Dow Chemical) | 20,000 g |
| Hydroxypropylcellulose (Klucel G marketed by Hercules) | 3000 g |
| Ethyl alcohol | 40,000 g |
| Minoxidil | 2000 g |
| Water qs | 100,000 g |

This thickened lotion was applied to the scalp, once or twice a day, at a rate of 1 ml per application.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regimen for promoting pigmentation of the skin and/or hair, comprising administering to an human in need of such treatment an effective tyrosinase activity-stimulating amount of at least one 6-substituted pyrimidine 3-oxide having the structural formula (I):

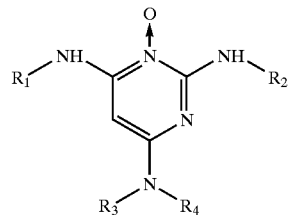

in which $R_1$ and $R_2$, which may be identical or different, are each a hydrogen atom or a $C_1$–$C_{12}$ alkyl radical; and $R_3$ and $R_4$, which may be identical or different, are each a $C_1$–$C_{12}$ alkyl radical or, when taken together, form a heterocycle with the nitrogen atom from which they depend, with the proviso that, when $R_3$ and $R_4$, taken together, form a piperidino ring, then at least one of the radicals $R_1$ or $R_2$ must be other than a hydrogen atom.

2. The regimen as defined by claim 1, comprising topically administering said at least one 6-substituted pyrimidine 3-oxide.

3. The regimen as defined by claim 1, comprising systemically administering said at least one 6-substituted pyrimidine 3-oxide.

4. The regimen as defined by claim 1, said at least one 6-substituted pyrimidine 3-oxide comprising 2,4-bis-methylamino-6-dimethylaminopyrimidine 3-oxide, 2,4-bis-ethylamino-6-dimethylaminopyrimidine 3-oxide, 2,4-bis-propylamino-6-dimethylaminopyrimidine 3-oxide, 2,4-bis-propylamino-6-piperidinopyrimidine 3-oxide, 2-amino-4-methylamino-6-piperidinopyrimidine 3-oxide, 2-amino-4-propylamino-6-piperidinopyrimidine 3-oxide, 2-amino-4-hexylamino-6-piperidinopyrimidine 3-oxide, 2-amino-4-benzylamino-6-piperidinopyrimidine 3-oxide, 2-amino-4-(2-hydroxyethylamino)-6-piperidinopyrimidine 3-oxide, 2-amino-4-propylamino-6-dimethylaminopyrimidine 3-oxide, 2-amino-4-butylamino-6-dimethylaminopyrimidine 3-oxide, or 2-amino-4-isopropylamino-6-dimethylaminopyrimidine 3-oxide.

5. The regimen as defined by claim 1, said at least one 6-substituted pyrimidine 3-oxide comprising 2-amino-4-propylamino-6-dimethylaminopyrimidine 3-oxide, 2-amino-4-methylamino-6-piperidinopyrimidine 3-oxide, 2,4-bis-propylamino-6-dimethylaminopyrimidine 3-oxide, 2,4-bis-propylamino-6-piperidinopyrimidine 3-oxide, 2,4-bis-methylamino-6-dimethylaminopyrimidine 3-oxide, or 2,4-bis-ethylamino-6-dimethylaminopyrimidine 3-oxide.

6. The regimen as defined by claim 1, comprising coadministering to said individual at least one substrate of at least one enzyme exhibiting tyrosinase activity.

7. The regimen as defined by claim 6, said at least one substrate comprising tyrosine or derivative thereof, or 3,4-dihydroxy-α-phenylalanine (DOPA).

* * * * *